United States Patent
Koga

(10) Patent No.: US 12,135,284 B2
(45) Date of Patent: Nov. 5, 2024

(54) IMAGE PROCESSING METHOD, IMAGE PROCESSING APPARATUS, IMAGING SYSTEM, AND STORAGE MEDIUM, FOR CONTENT CONCENTRATION ESTIMATION

(71) Applicant: CANON KABUSHIKI KAISHA, Tokyo (JP)

(72) Inventor: Hironobu Koga, Utsunomiya (JP)

(73) Assignee: CANON KABUSHIKI KAISHA, Tokyo (JP)

(*) Notice: Subject to any disclaimer, the term of this patent is extended or adjusted under 35 U.S.C. 154(b) by 436 days.

(21) Appl. No.: 17/532,206

(22) Filed: Nov. 22, 2021

(65) Prior Publication Data
US 2022/0082499 A1    Mar. 17, 2022

Related U.S. Application Data
(63) Continuation of application No. PCT/JP2020/016789, filed on Apr. 16, 2020.

(30) Foreign Application Priority Data
May 28, 2019 (JP) ................. 2019-099129

(51) Int. Cl.
*G01N 21/55* (2014.01)
*G01N 33/00* (2006.01)
(Continued)

(52) U.S. Cl.
CPC ......... *G01N 21/55* (2013.01); *G01N 33/0098* (2013.01); *G06T 7/90* (2017.01); *H04N 23/71* (2023.01); *G06T 2207/10024* (2013.01)

(58) Field of Classification Search
CPC ............. G01N 21/55; G01N 33/0098; G01N 2021/8466; G01N 2201/0616;
(Continued)

(56) References Cited

U.S. PATENT DOCUMENTS

| | | | |
|---|---|---|---|
| 5,898,175 A | 4/1999 | Hirabayashi | |
| 6,114,683 A | 9/2000 | Spiering et al. | |

(Continued)

FOREIGN PATENT DOCUMENTS

| | | |
|---|---|---|
| CN | 1286898 A | 3/2001 |
| CN | 106954385 A | 7/2017 |

(Continued)

OTHER PUBLICATIONS

"Madain Perez-Patricio et. al., Optical Method for Estimating the Chlorophyll Contents in Plant Leaves, Feb. 2018, Sensors 2018, 18[2], 650" (Year: 2018).*

(Continued)

*Primary Examiner* — Andrae S Allison
*Assistant Examiner* — Phuong Hau Cai
(74) *Attorney, Agent, or Firm* — Carter, DeLuca & Farrell LLP

(57) ABSTRACT

An image processing method includes acquiring an image obtained by imaging of an object, ambient light data during the imaging, and reflection characteristic data and transmission characteristic data which depend on a concentration of a material contained in the object, and separating a reflected light component and a transmitting light component in the image using the ambient light data, the reflection characteristic data, and the transmission characteristic data.

15 Claims, 12 Drawing Sheets

GRAYSCALE IMAGE

REFLECTED LIGHT COMPONENT COEFFICIENT

(51) Int. Cl.
*G06T 7/90* (2017.01)
*H04N 23/71* (2023.01)

(58) Field of Classification Search
CPC .. G01N 2201/1244; G01N 21/25; G06T 7/90; G06T 2207/10024; H04N 23/71
See application file for complete search history.

(56) References Cited

U.S. PATENT DOCUMENTS

| | | | |
|---|---|---|---|
| 9,651,722 | B2 | 5/2017 | Ito et al. |
| 2008/0239293 | A1 | 10/2008 | Fuchigami et al. |
| 2018/0018537 | A1 | 1/2018 | Kim et al. |

FOREIGN PATENT DOCUMENTS

| | | |
|---|---|---|
| JP | 2002-168771 A | 6/2002 |
| JP | 2004-301810 A | 10/2004 |
| JP | 2018-151832 A | 9/2018 |
| WO | 2011/093024 A1 | 8/2011 |
| WO | 2016/181743 A1 | 11/2016 |
| WO | 2018/180954 A1 | 10/2018 |

OTHER PUBLICATIONS

"Farshad Vesali et. al., Development of an android app to estimate chlorophyll content of corn leaves based on contact imaging, Aug. 2015, Computers and Electronics in Agriculture, vol. 116, pp. 211-220" (Year: 2015).*

"Chappelle EW et. al., Ratio analysis of reflectance spectra (RARS): An algorithm for the remote estimation of the concentrations of chlorophyll a, chlorophyll b, and carotenoids in soybean leaves., 1992 Remote Sens Environ 39: 239-247" (Year: 1992).*

"Anatoly A. Gitelson et. al., Signature Analysis of Leaf Reflectance Spectra: Algorithm Development for Remote Sensing of Chlorophyll, 1996, J. Plant Physiol, vol. 148, pp. 494-500" (Year: 1996).*

Zhang, Y. et al., "Leaf chlorophyll content retrieval from airborne hyperspectral remote sensing imagery" Remote Sensing of Environment (Jul. 2008) pp. 3234-3247, vol. 112, No. 7, XP22709018.

Kim, Y. et al., "Ambient Illumination Effect on a Spectral Image Sensor for Detecting Crop Nitrogen Stress" ASAE Meeting Presentation (Jul. 2001) pp. 1-8, XP08069463.

Extended European Search Report issued by the European Patent Office on Dec. 21, 2022 in corresponding EP Patent Application No. 20812894.2.

Wang, Shipan, "Information optical theory and application" Beijing University of Posts and Telecommunications Press, (Mar. 31, 2004) pp. 148, with English abstract.

Chinese Office Action issued in CN Application No. 202080038049.X, dated Jun. 17, 2023, with English translation.

International Search Report issued by the Japan Patent Office on Jun. 30, 2020 in corresponding International Application No. PCT/JP2020/016789, with English translation.

* cited by examiner

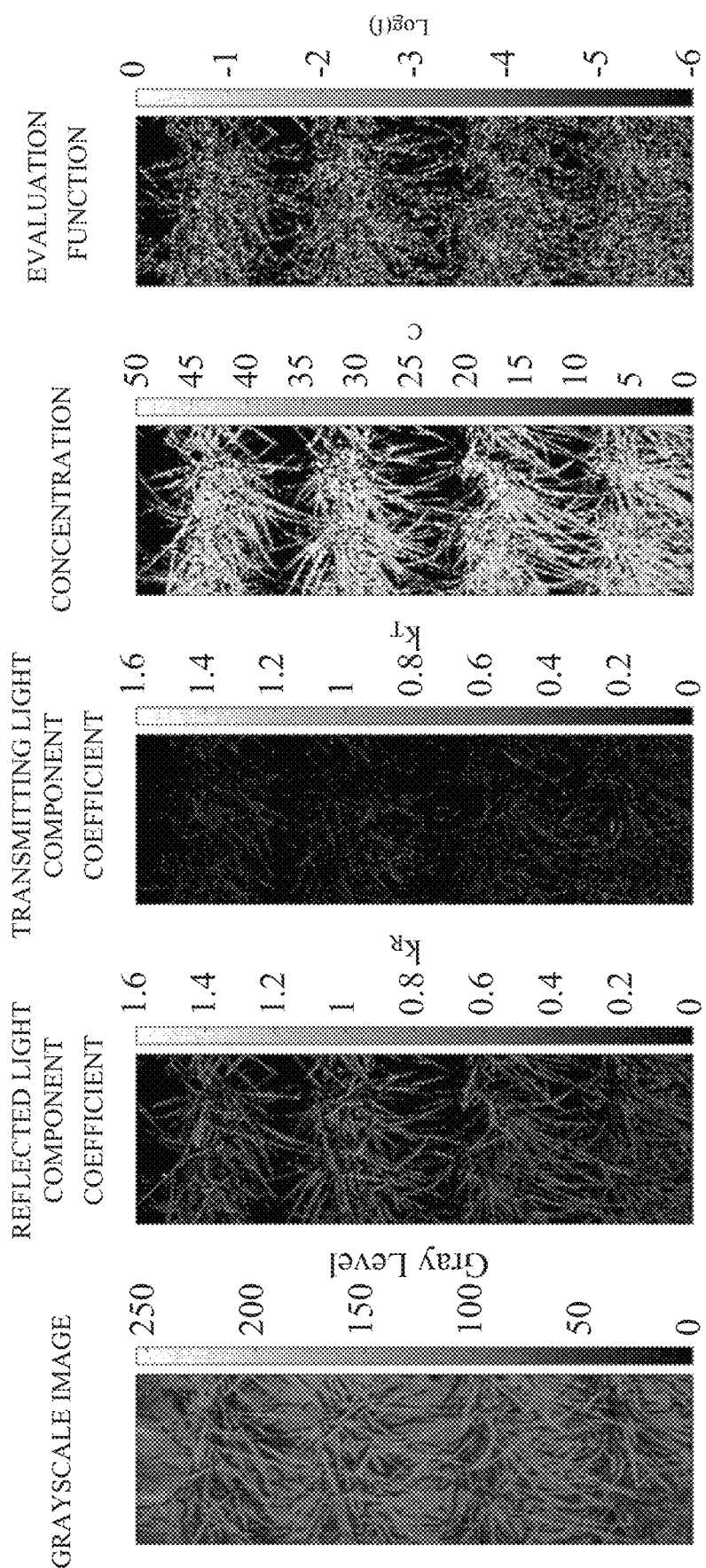

IMAGE PROCESSING METHOD, IMAGE PROCESSING APPARATUS, IMAGING SYSTEM, AND STORAGE MEDIUM, FOR CONTENT CONCENTRATION ESTIMATION

CROSS-REFERENCE TO RELATED APPLICATIONS

This application is a Continuation of International Patent Application No. PCT/JP2020/016789, filed on Apr. 16, 2020, which claims the benefit of Japanese Patent Application No. 2019-099129, filed on May 28, 2019, both of which are hereby incorporated by reference herein in their entirety.

BACKGROUND OF THE INVENTION

Field of the Invention

The present invention relates to an image processing method that estimates a concentration of a material included in an object from a spectral image.

Description of the Related Art

There has recently proposed a method for estimating a leaf color index using the remote sensing technology for efficient and labor-saving agricultural work. For example. Patent Document 1 discloses a method of estimating a SPAD (Soil & Plant Analyzer Development) value from a spectral measurement result of light reflected by a plant.

The method disclosed in Japanese Patent Laid-Open No. ("JP") 2002-presumes that the light that has reached a light receiver is only the light reflected by the plant. However, the leaf of the plant is a semitransparent object and thus transmitting light transmitting through the leaf of the plant also reaches the light receiver as well as the reflected light reflected by the leaf of the plant. In addition, a mixture ratio of the reflected light and the transmitting light changes according to the weather (sunny, cloudy, etc.) and the position of the sun (altitude and azimuth). Therefore, the method disclosed in JP 2002-168771 has difficulty in highly accurately estimate the concentration of the material (leaf color, that is, the SPAD value), because the mixture ratio of the reflected light and the transmitting light changes as the weather or the sun position changes.

SUMMARY OF THE INVENTION

The present invention provides an image processing method, an image processing apparatus, an imaging system, and a program, each of which can highly accurately estimate a concentration of a material contained in an object from a spectral image.

An image processing method according to one aspect of the present invention includes acquiring an image obtained by imaging of an object, ambient light data during the imaging, and reflection characteristic data and transmission characteristic data which depend on a concentration of a material contained in the object, and separating a reflected light component and a transmitting light component in the image using the ambient light data, the reflection characteristic data, and the transmission characteristic data.

An image processing apparatus according to another aspect of the present invention includes at least one processor or circuit configured to execute a plurality of tasks including an acquiring task of acquiring an image obtained by imaging of an object, ambient light data during the imaging, and reflection characteristic data and transmission characteristic data which depend on a concentration of a material contained in the object, and a separating task of separating a reflected light component and a transmitting light component in the image using the ambient light data, the reflection characteristic data, and the transmission characteristic data.

An imaging system according to another aspect of the present invention includes an image capturer configured to capture an object, a detector configured to detect ambient light data when the object is captured by the image capturer, and the image processing apparatus.

A non-transitory computer-readable storage medium storing a program according to another aspect of the present invention causes a computer to execute the image processing method.

Further features of the present invention will become apparent from the following description of exemplary embodiments with reference to the attached drawings.

BRIEF DESCRIPTION OF THE DRAWINGS

FIGS. 7A to 7E show results of the separation processing according to the first embodiment.

DESCRIPTION OF THE EMBODIMENTS

Figure 1:
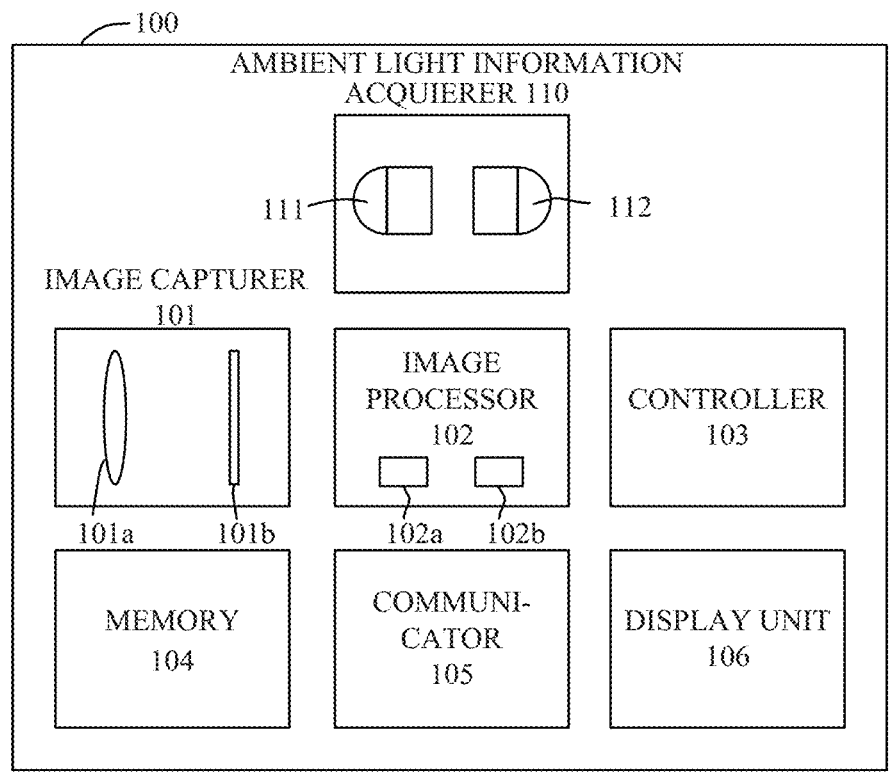
FIG. 1 is a block diagram of an image processing system according to a first embodiment.

Referring now to the accompanying drawings, a detailed description will be given of embodiments according to the present invention. Corresponding elements in respective figures will be designated by the same reference numerals, and a duplicate description thereof will be omitted.

First Embodiment

Figure 2:
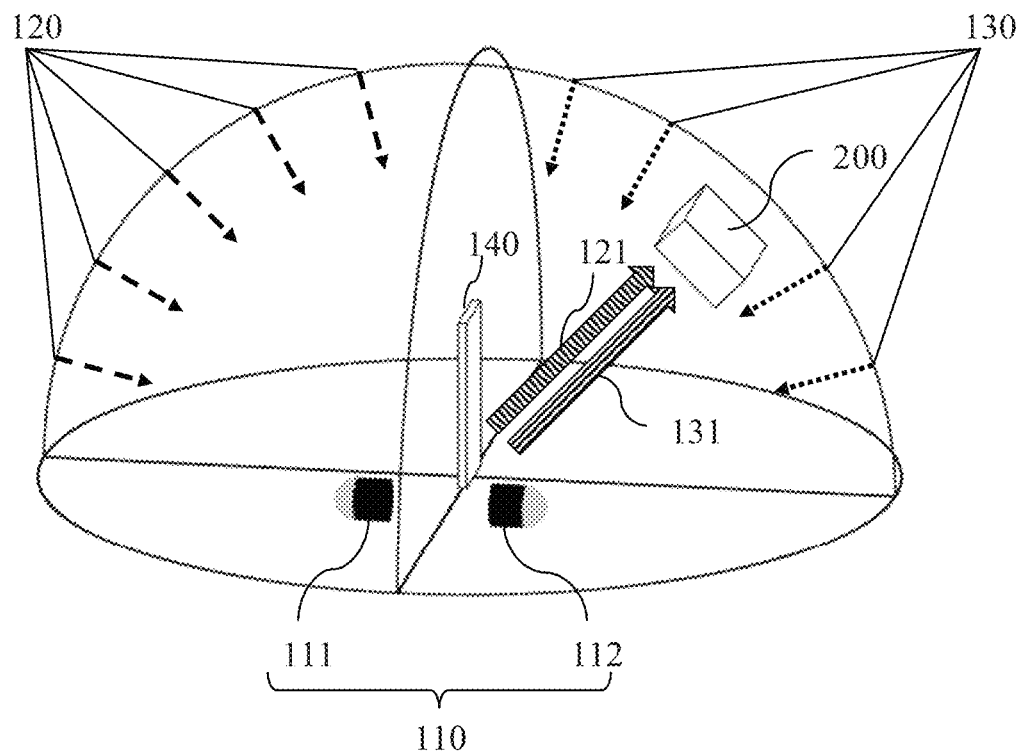
FIG. 2 is an explanatory diagram of a camera captured model according to the first embodiment.

Referring now to FIG. 2, a description will be given of a camera captured model according to a first embodiment of the present invention. FIG. 2 is an explanatory diagram of a camera captured model according to this embodiment. FIG. 2 illustrates an object 140 to be captured by a camera (image pickup apparatus) 200. The object 140 is illuminated by ambient light incident on the object 140 from each position on a hemispherical space in which the object 140 is placed. In FIG. 2, the ambient light is divided into ambient light 120 that illuminates the back surface of the object 140 and ambient light 130 that illuminates the front surface of the object 140.

The object 140 is a semitransparent object, the ambient light 120 is diffused and absorbed inside the object 140, and part of transmitting light (transmitting light 121) reaches the camera 200. On the other hand, the ambient light 130 is diffused and absorbed inside the object 140, and part of the reflected light (reflected light 131) reaches the camera 200. In this embodiment, the so-called diffuse reflected light reflected by such a process will be simply referred to as reflected light, and is distinguished from regular reflection light reflected on the surface of the object 140.

Therefore, the image of the object 140 captured by the camera 200 is formed by a mixture of transmitting light (transmitting light component) 121 and reflected light (reflected light component) 131 at a specific ratio. The mixture ratio of the transmitting light 121 and the reflected light 131 changes as the ambient lights 120 and 130 fluctuate. In particular, in imaging under outdoor ambient light, the mixture ratio of the transmitting light 121 and the reflected light 131 changes depending on the weather (sunny, cloudy, etc.) and the sun position (altitude and azimuth).

When the image is captured under the outdoor ambient light in this way, the mixture ratio of the transmitting light 121 and the reflected light 131 is unknown and changes depending on the illumination environment during imaging. Therefore, it is difficult to quantitatively estimate the concentration of the material (chlorophyll or the like) contained in the object from the image captured in such a state. This embodiment can quantitatively estimate the concentration of the material contained in the object by separating the transmitting light 121 and the reflected light 131 (separation processing) from the spectral image captured under such ambient light. Hereinafter, the separation processing will be described in detail.

First, this embodiment formulates the camera captured model illustrated in FIG. 2, for example, as in the expression (1).

$$I_n = I_{R,n} + I_{T,n} = k_R I_{R_0,n} R_n(c) + k_T I_{T_0,n} T_n(c) \quad (1)$$

In the expression (1), $I_n$ represents a luminance value of an image (spectral image) captured by the camera 200, and a subscript n represents a wavelength number of the spectral image. For example, when the camera 200 is an RGB camera, n={1, 2, 3}, and $I_1$, $I_2$, and $I_3$ each indicate RGB luminance values. $I_{R,n}$ and $I_{T,n}$ represent luminance values when the reflected light 131 and the transmitting light 121 are acquired independently. $I_{R_0,n}$ and $I_{T_0,n}$ represent the illuminances of the ambient lights 130 and 120 that illuminate the object 140, respectively. $R_n(c)$ and $T_n(c)$ represent spectral reflection characteristics (reflection characteristic data) and spectral transmission characteristics (transmission characteristic data), respectively, depending on the concentration c of the material contained in the object 140. In this embodiment, each of the spectral reflection characteristic $R_n(c)$ and the spectral transmission characteristic $T_n(c)$ has previously been stored as known library data in a storage device such as a memory. $k_R$ represents a ratio of the ambient light 130 reflected by the object 140 and reaching the camera 200, and $k_T$ represents a ratio of the ambient light 120 passing through the object 140 and reaching the camera 200.

The illuminance information $I_{R_0,n}$, and the illuminance information $I_{T_0,n}$ of the ambient lights 130 and 120 during imaging are known and acquired, for example, by the ambient light information acquirer (detector) 110 illustrated in FIG. 2. In this embodiment, the ambient light information acquirer 110 includes an ambient light sensor (first ambient light sensor) 111 and an ambient light sensor (second ambient light sensor) 112 installed in two different directions. The ambient light sensor 111 acquires the illuminance information $I_{T_0,n}$ of the ambient light 120. The ambient light sensor 112 acquires the illuminance information $I_{R_0,n}$ of the ambient light 130.

This embodiment acquires the ratio $k_R$ of the reflected light (reflected light component), the ratio $k_T$ of the transmitting light (transmitting light component), and the concentration c of the material contained in the object 140 by performing the optimization (optimization calculation) represented by the following expression (2) using the camera captured model formulated in this way.

$$\min_{k_R k_T, c} \sum_{n=1}^{L} \left\| I_n - \left( k_R I_{R_0,n} R_n(c) + k_T I_{T_0,n} T_n(c) \right) \right\|_2 \quad (2)$$

In this expression (2), "$\| \ \|2$" represents the L2 norm. The separation processing according to this embodiment means the execution of the optimization calculation of the expression (2), but the present invention is not limited to this example. With $k_R$, $k_T$, and c obtained by the optimization, the reflected light (reflected light component) and the transmitting light (transmitting light component) are separated and expressed as illustrated in the following expressions (3) and (4), respectively.

$$I_{R,n} = k_R I_{R_0,n} R_n(c) \quad (3)$$

$$I_{T,n} = k_T I_{T_0,n} T_n(c) \quad (4)$$

Therefore, this embodiment can separate the transmitting light 121 and the reflected light 131 from the spectral image in which the transmitting light 121 and the reflected light 131 are mixed at an unknown mixture ratio. Further, this embodiment can quantitatively estimate the concentration of the material contained in the object 140.

This embodiment relates to an image processing system (imaging system) that estimates the concentration of the object (paddy rice leaf) 140 from the image (spectral image) acquired by the camera (RGB camera) 200. In this embodiment, the concentration c in the expression (2) corresponds to the SPAD value.

Referring now to FIG. 1, a description will be given of the configuration of the image processing system 100 according to this embodiment. FIG. 1 is a block diagram of the image processing system 100. The image processing system 100 includes an image capturer 101, an image processor (image processing apparatus) 102, a controller 103, a memory 104, a communicator 105, a display unit 106, and an ambient light information acquirer 110. The image capturer 101 includes an imaging optical system 101a and an image sensor 101b. The image sensor 101b photoelectrically converts an optical image (object image) formed via the imaging optical system 101a and outputs an image (image data)

to the image processor 102. The image processor 102 has an acquiring means (task) 102a and a separating means (task) 102b.

The image processing system 100 can be provided inside the camera 200. Alternatively, some functions such as the image processor 102 of the image processing system 100 may be implemented in a computer (user PC) away from the camera 200 or on cloud computing. In this case, the camera 200 has only part of the image processing system 100 including the image capturer 101.

FIG. 2 illustrates the object 140 that is imaged under outdoor ambient light using the image processing system 100. As illustrated in FIG. 2, the ambient light information acquirer 110 of the image processing system 100 includes an ambient light sensor 111 configured to acquire the illuminance incident on the back surface of the object 140, and an ambient light sensor 112 configured to acquire the illuminance incident on the front surface of the object 140.

Figure 3:
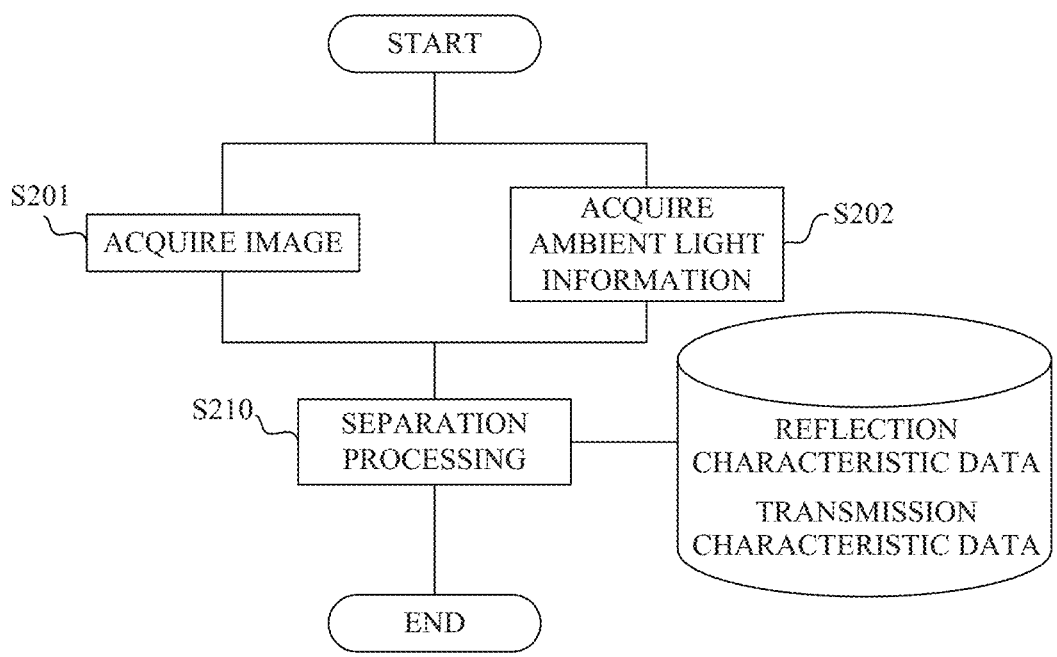
FIG. 3 is a flowchart of an image processing method according to the first embodiment.

Referring now to FIG. 3, a description will be given of an image processing method according to this embodiment. FIG. 3 is a flowchart of the image processing method according to this embodiment. Each step in FIG. 3 is mainly executed by the acquiring means 102a or the separating means 102b in the image processor 102.

First, in the step S201, the image capturer 101 in the image processing system 100 images the object 140 by the signal from the controller 103 and acquires an RGB image (spectral image). Then, the acquiring means 102a in the image processor 102 acquires the image captured by the image capturer 101. At the same time as the step S201, in the step S202, the ambient light information acquirer 110 (ambient light sensors 111 and 112) acquires (detects), based on the signal from the controller 103, the ambient light information (ambient light data) $I_{R0,n}$ and $I_{T0,n}$. In this embodiment, the ambient light information is information on the tint. Then, the acquiring means 102a acquires the ambient light information $I_{R0,n}$ and $I_{T0,n}$ detected by the ambient light information acquirer 110.

The ambient light sensors 111 and 112 is made by disposing a diffuser on a sensor having the same spectral sensitivity characteristic as that of the image capturer 101, and acquire ambient light information having the same spectral wavelength as that of the image capturer 101. The ambient light sensors 111 and 112 may include a spectroradiometer, and acquire the ambient light information $I_{R0,n}$ and $I_{T0,n}$ using the following expressions (5) and (6) with an acquired spectral irradiance $E(\lambda)$, a spectral transmittance characteristic $L(\lambda)$ of the imaging optical system, and a spectral sensitivity characteristic $Sn(\lambda)$ of the image sensor.

$$I_{T_0,n} = \int_{\lambda_{n,1}}^{\lambda_{n,2}} E_T(\lambda,c) L(\lambda) S_n(\lambda) d\lambda \quad (5)$$

$$I_{R_0,n} = \int_{\lambda_{n,1}}^{\lambda_{n,2}} E_R(\lambda,c) L(\Delta) S_n(\lambda) d\lambda \quad (6)$$

In the expressions (5) and (6), $E_T(\lambda)$ is the illuminance of the ambient light 120, $E_R(\lambda)$ is the illuminance of the ambient light 130, and $\lambda_{n,1}$ and $\lambda_{n,2}$ are the shortest wavelength and the longest wavelength, respectively, in the wavelength band in which the image sensor 101b having the spectral sensitivity characteristic $S_n(\lambda)$ has sensitivity.

Figure 4:
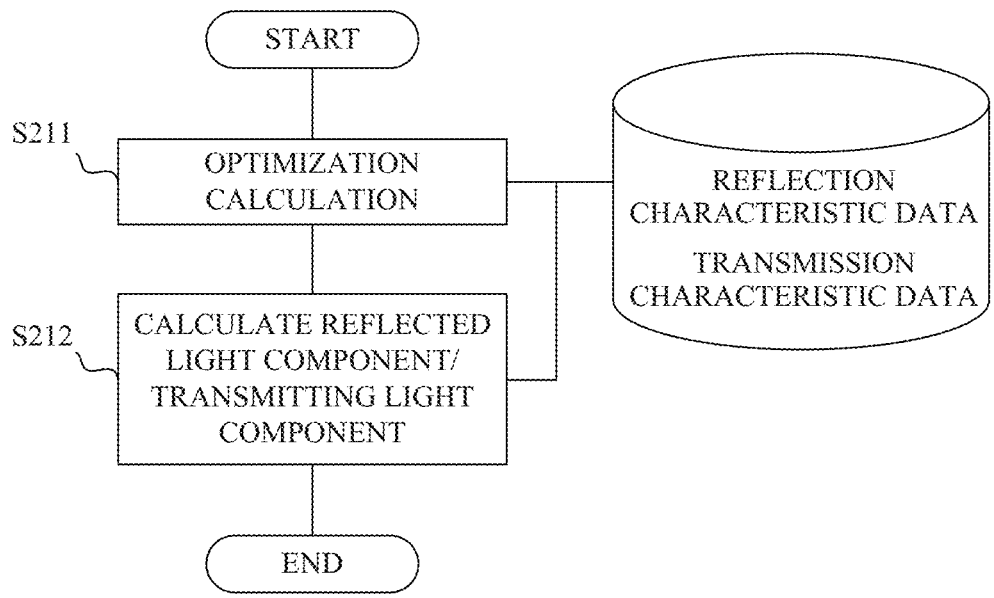
FIG. 4 is a flowchart of separation processing according to the first embodiment.

Next, in the step S210, the separating means 102b in the image processor 102 performs separation processing based on the expression (2). Referring now to FIG. 4, a description will be given of the separation processing according to this embodiment. FIG. 4 is a flowchart of the separation processing according to this embodiment. Each step in FIG. 4 is mainly executed by the separating means 102b in the image processor 102.

First, in the step S211 the separating means 102b performs an optimization calculation based on the expression (2). Next, in the step S212, the separating means 102b calculates the reflected light component and transmitting light component of the expressions (3) and (4). In the steps S211 and S212, the separating means 102b utilizes the reflection characteristic data and the transmission characteristic data of the object that have been previously stored.

Figures 5A, 5B:
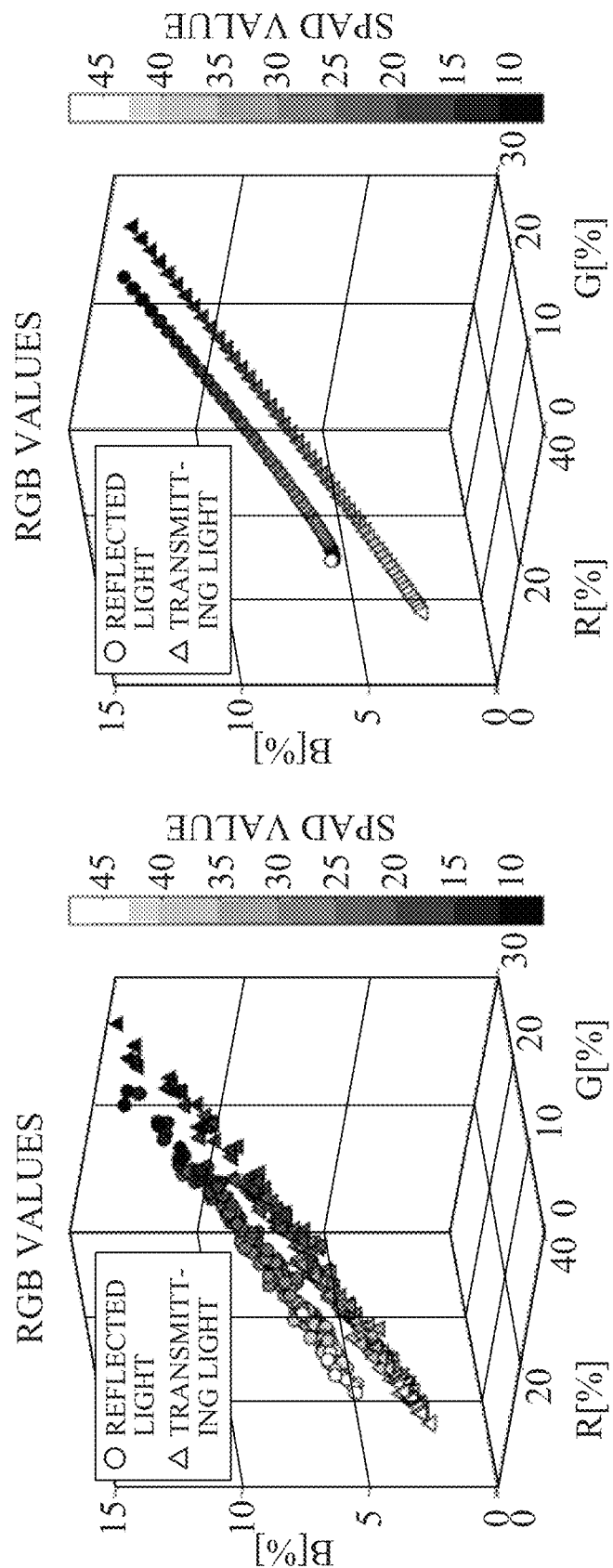
FIGS. 5A and 5B are explanatory diagrams of reflection characteristic data and transmission characteristic data according to the first embodiment.

Referring not to FIGS. 5A and 5B, a description will be given of the reflection characteristic data and the transmission characteristic data in this embodiment. FIGS. 5A and 5B are explanatory diagrams of reflection characteristic data and transmission characteristic data. FIG. 5A is data showing SPAD value dependencies on the RGB reflectance and the RGB transmittance that have been acquired in advance. A dot plotted point represents the RGB reflectance, a triangularly plotted point represents the RGB transmittance, and a filled color corresponds to the SPAD value. This embodiment separates, as illustrated in FIG. 5A, the reflected light and the transmitting light utilizing the fact that the spectral reflection characteristic and the spectral transmission characteristic have different characteristics from each other.

FIG. 5B plots the results of fitting the RGB reflectance and RGB transmittance of FIG. 5A into the following expressions (7) and (8) by the least squares method using the SPAD value c as a parameter.

$$R_n(c) = \sum_{i=0}^{N} a_{n,i} \cdot c^i \quad (7)$$

$$T_n(c) = \sum_{i=0}^{N} b_{n,i} \cdot c^i \quad (8)$$

In expressions (7) and (8), $a_{n,i}$ and $b_{n,i}$ are constants determined by the least squares method. In FIG. 5B, similar to FIG. 5A, a dot plotted point represents the RGB reflectance, and a triangularly plotted point represents the RGB transmittance.

Figures 6A, 6B:
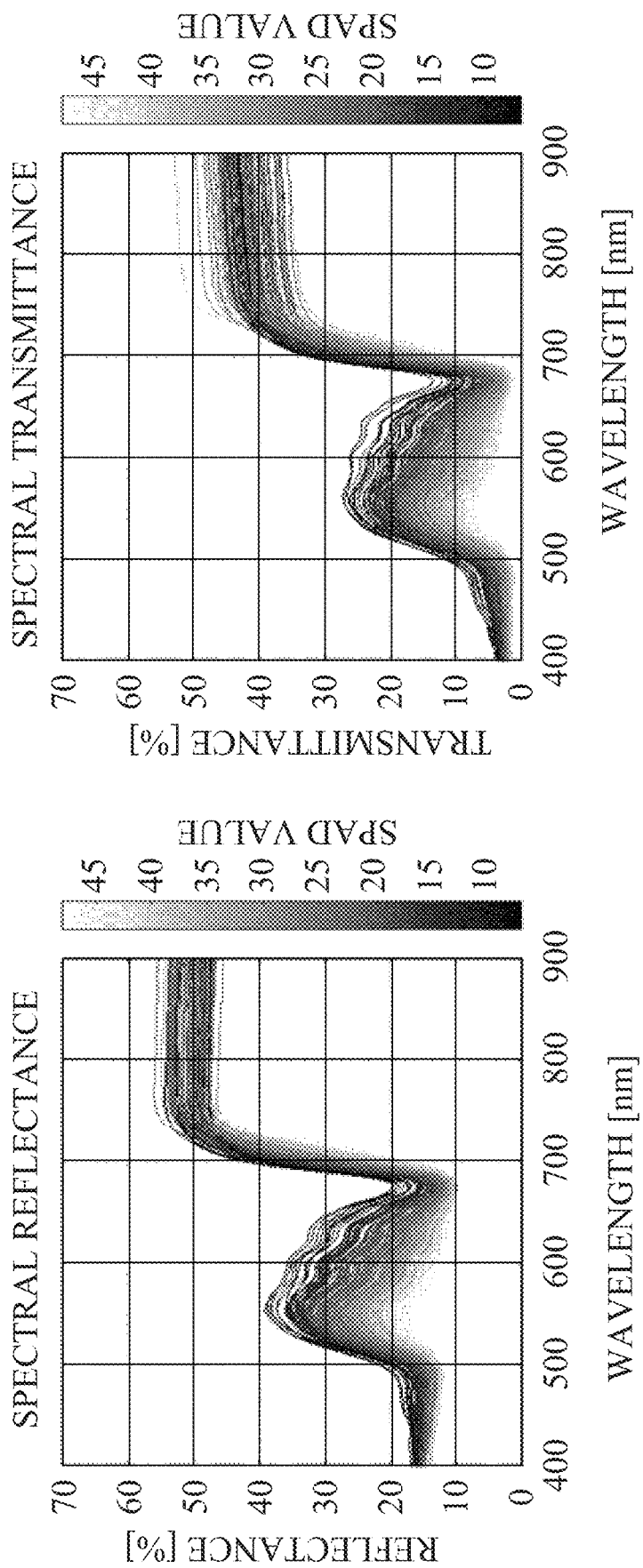
FIGS. 6A and 6B are explanatory diagrams of other reflection characteristic data and transmission characteristic data according to the first embodiment.

This embodiment has stored information on the expressions (7) and (8) as the reflection characteristic data and the transmission characteristic data of the object, respectively. The reflection characteristic data and the transmission characteristic data are not limited to the above data. For example, as illustrated in FIGS. 6A and 6B, the reflectance characteristic Rfl(c, $\lambda$) and the transmittance characteristic Trs(c, $\lambda$) of the object may be used. FIGS. 6A and 6B is an explanatory diagram of other reflection characteristic data and transmission characteristic data according to this embodiment. FIG. 6A illustrates a spectral reflectance characteristic of the paddy rice leaf, where the abscissa axis represents a wavelength and the ordinate axis represents a reflectance. The color of each line corresponds to the SPAD value shown on the color bar. Similarly, FIG. 6B illustrates the transmittance characteristic of paddy rice, where the abscissa axis represents a wavelength and the ordinate axis illustrates a transmittance.

When the reflection characteristic data and the transmission characteristic data as illustrated in FIGS. 6A and 6B are used, $R_n(c)$ and $T_n(c)$ are preferably calculated using the following expressions (9) and (10) with the spectral transmittance characteristic $L(\lambda)$ of the imaging optical system 101a and the spectral sensitivity characteristic $Sn(\lambda)$ of the image sensor 101b.

$$R_n(c) = \sum_{\lambda_{n,1}}^{\lambda_{n,2}} \text{Rfl}(c,\lambda) L(\lambda) S_n(\lambda) d\lambda \quad (9)$$

$$T_n(c) = \int_{\lambda_{n,1}}^{\lambda_{n,2}} \text{Trs}(c,\lambda) L(\lambda) S_n(\lambda) d\lambda \quad (10)$$

In expressions (9) and (10), $\lambda_{n,1}$ and $\lambda_{n,2}$ are the shortest wavelength and the longest wavelength, respectively, in the wavelength band in which the image sensor 101*b* having the spectral sensitivity characteristic Sn(λ) has sensitivity.

In the step S211 the separating means 102*b* performs the optimization calculation of the expression (2) using the spectral image, the ambient light information, and the reflection characteristic data and the transmission characteristic data of the object 140 stored in the memory 104. The optimization calculation can use a known optimization method, such as a gradient method. As illustrated in the expressions (7) and (8), when $R_n(c)$ and $T_n(c)$ are differentiable functions, the expression (2) is also a differentiable function and thus a faster optimization calculation method such as the Newton method and the trust region method can be used.

Referring now to FIGS. 7A to 7E, a description will be given of results of the separation processing by the optimization calculation. FIGS. 7A to 7E show the results of the separation processing according to this embodiment and the result of performing the optimization calculation using a trust region method in the step S211 in FIG. 4. FIG. 7A is an image made by converting an RGB image of paddy rice captured by an RGB camera into a grayscale image. FIGS. 7B to 7D are diagrams showing the results of optimizing calculations for the ratio $k_R$ of the reflected light, the ratio $k_T$ of the transmitting light, and the concentration c of the material for each pixel of the paddy rise leaf. FIG. 7E is a diagram showing a value f of the optimization evaluation function of the expression (2) on a logarithmic scale.

In the step S212 in FIG. 4, the separating means 102*b* calculates the reflected light component and the transmitting light component based on the expressions (3), (4), (7), and (8) from the ratio $k_R$ of the reflected light, the ratio $k_T$ of the transmitting light, and the material concentration c obtained in the step S211. As described above, this embodiment can separate the reflected light component and the transmitting light component from the spectral image of the object. In the processing of calculating the expression (2), the material concentration c of the object 140 can be estimated.

Second Embodiment

Next follows a description of a second embodiment according to the present invention. This embodiment estimates a SPAD value of a rice leaf from the spectral image acquired by the RGB camera in the same manner as in the first embodiment.

Figure 8:
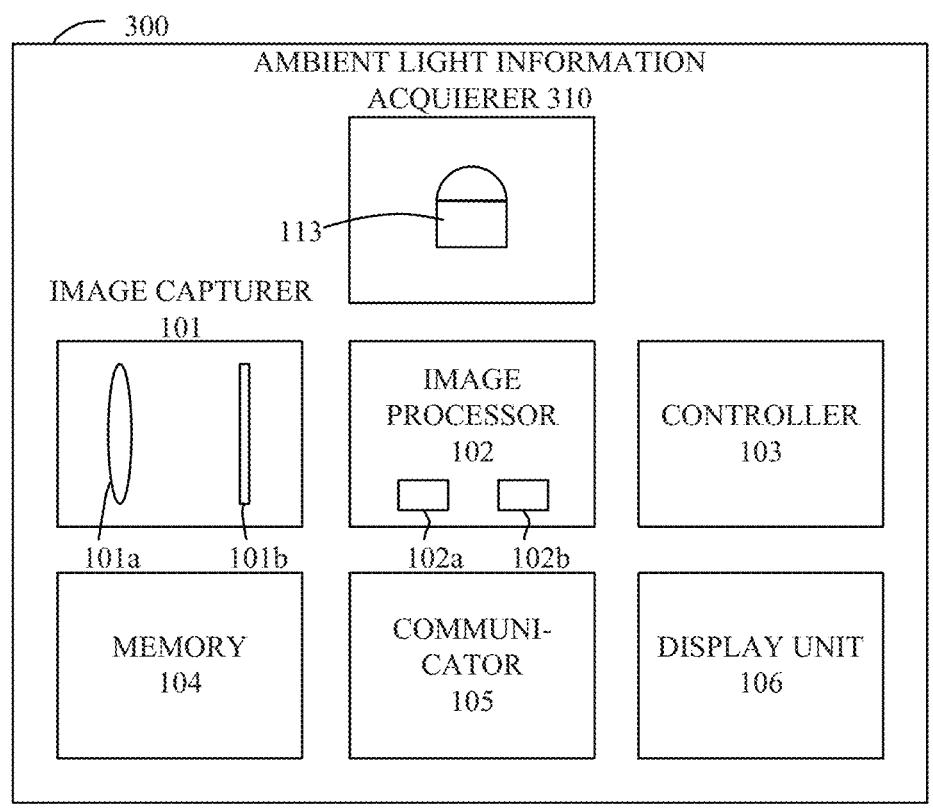
FIG. 8 is a block diagram of an image processing system according to a second embodiment.
Figure 9:
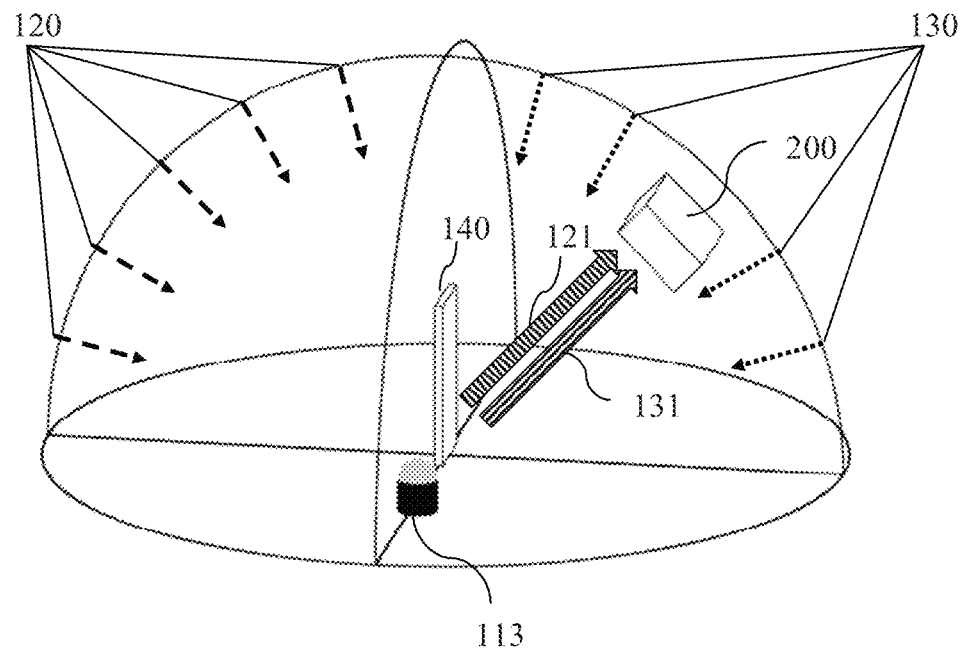
FIG. 9 is an explanatory diagram of a camera captured model according to the second embodiment.

Referring now to FIGS. 8 and 9, a description will be given of a configuration of an image processing system 300 and the camera captured model according to this embodiment. FIG. 8 is a block diagram of the image processing system 300. FIG. 9 is an explanatory diagram of the camera captured model, and illustrates the object 140 that is captured under outdoor ambient light using the image processing system 300. The image processing system 300 according to this embodiment is different from the image processing system 100 according to the first embodiment having an ambient light information acquirer 110 in that the image processing system 300 includes an ambient light information acquirer (detector) 310. As illustrated in FIGS. 8 and 9, the ambient light information acquirer 310 exclusively includes a single ambient light sensor 113. Since the other configuration of the image processing system 300 is the same as that of the image processing system 100, a description thereof will be omitted.

Figure 10:
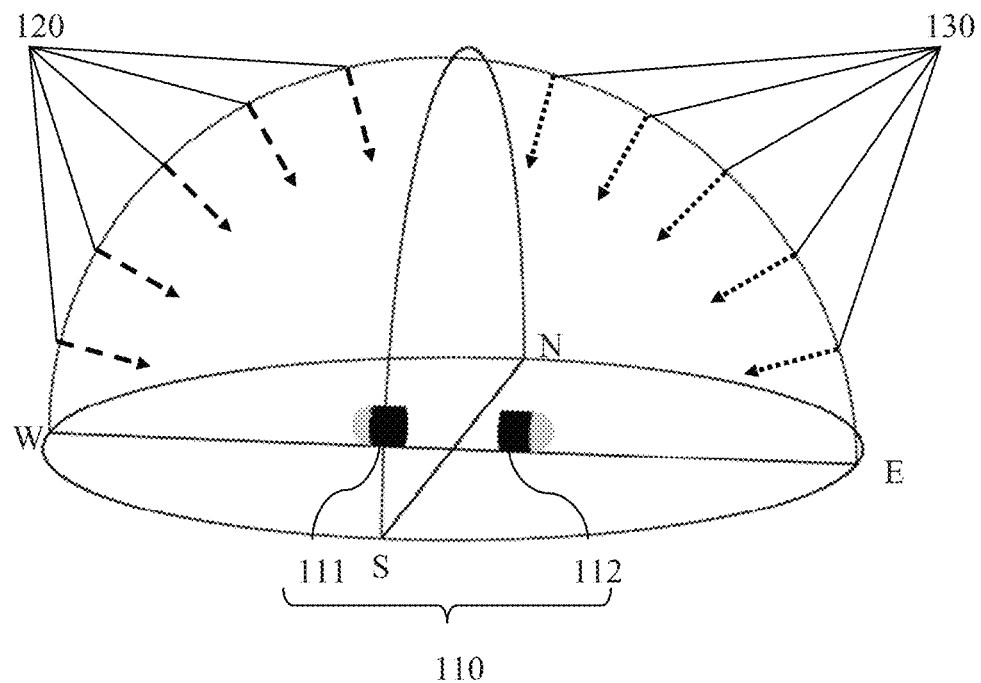
FIG. 10 is an explanatory diagram of a model for acquiring ambient light information according to the second embodiment.

Next follows a description of the reason for using only one ambient light sensor 113 in this embodiment. FIG. 10 is an explanatory diagram of the ambient light information acquiring model in this embodiment, and illustrates the arrangement of the ambient light sensor 111 arranged westward and the ambient light sensor 112 arranged eastward. The ambient light sensors 111 and 112 have a configuration in which a diffuser plate is attached to an RGB color sensor.

Figures 11A, 11B:
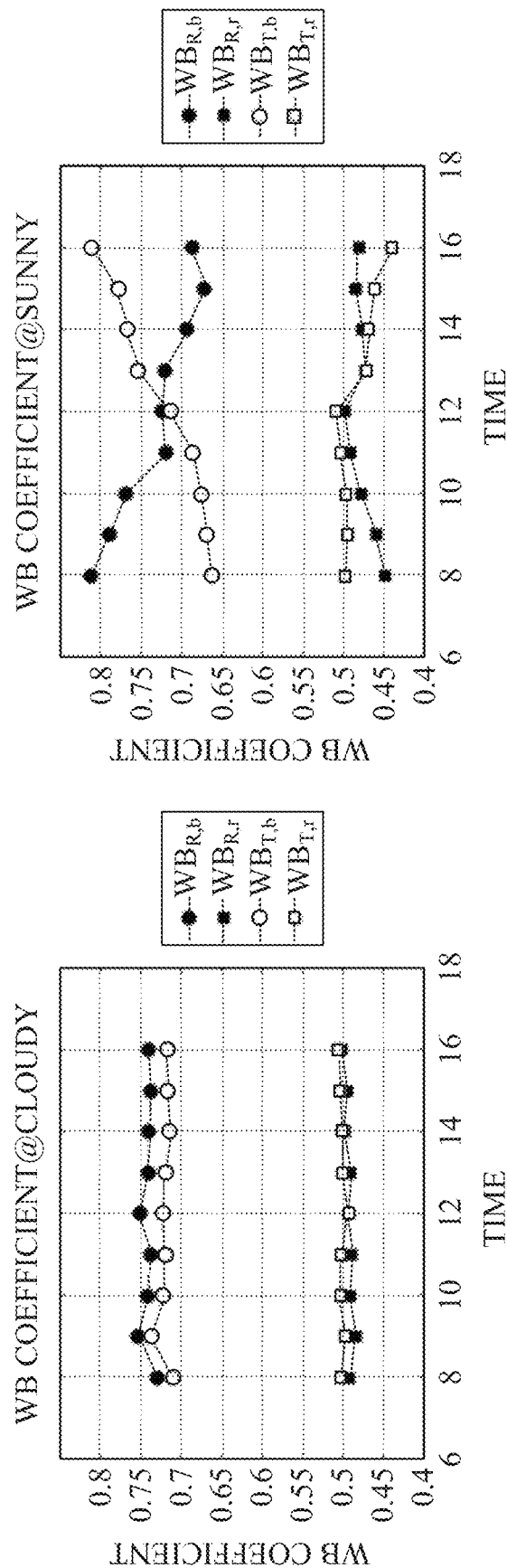
FIGS. 11A and 11B are explanatory diagrams of a time change of the ambient light information according to the second embodiment.

FIGS. 11A and 11B are explanatory diagrams of a time change of the ambient light information, and plots the ambient light information acquired by the ambient light sensors 111 and 112. In FIGS. 11A and 11B, $WB_{R,b}$, $WB_{R,r}$, $WB_{T,b}$, and $WB_{T,r}$ rare white balance correction coefficients calculated using the following expressions (11) to (14) with the illuminance information $I_{R0,n}$ acquired by the ambient light sensor 112 and the illuminance information $I_{T0,n}$ acquired by the ambient light sensor 111. n={1, 2, 3}, indicating that the values are acquired by the color sensors of R, G, and B in this order.

$$WB_{R,b} = I_{R_0,2}/I_{R_0,3} \tag{11}$$

$$WB_{R,r} = I_{R_0,2}/R_{0,1} \tag{12}$$

$$WB_{T,b} = I_{T_0,2}/I_{T_0,3} \tag{13}$$

$$WB_{T,r} = I_{T_0,2}/I_{T_0,1} \tag{14}$$

FIG. 11A is a diagram that plots the time change of the white balance correction coefficient when it is cloudy. A black dot represents $WB_{R,b}$, a white dot represents $WB_{T,b}$, a black square represents $WB_{R,r}$, and a white square represents $WB_{T,r}$. As illustrated in FIG. 11A, when it is cloudy, $WB_{R,b}$ and $WB_{T,b}$ are equal to each other and $WB_{R,r}$ and $WB_{T,r}$ are equal to each other regardless of the arrangement orientation of the ambient light sensor. FIG. 11B is a diagram that plots the time change of the white balance correction coefficient when it is sunny in the same manner as in FIG. 11A. When it is sunny. $WB_{R,b}$ and $WB_{T,b}$ are equal to each other and $WB_{R,r}$ and $WB_{T,r}$ are equal to each other at only around midday when the sun crosses the meridian.

Accordingly, this embodiment captures a spectral image when the white balance correction coefficient does not depend on the arrangement orientation of the ambient light sensor (such as within 2 hours before and after the sun crosses the meridian). Thereby, even the single ambient light sensor 113 can execute the separation processing of the reflected light and the transmitting light.

At such a time (such as within 2 hours before and after the sun crosses the meridian), the white balance correction coefficient does not depend on the orientation of the ambient light sensor. Therefore, the ambient light sensor 113 according to this embodiment is installed upwardly, for example, as illustrated in FIG. 9, and can acquire the ambient light information. Where $I_{R0,n}$ is the ambient light information acquired by the ambient light sensor 113 and $I_{T0,c} = m \cdot I_{R0,c}$ (m is a proportional constant), the expression (2) for the optimization calculation can be transformed as in the expression (15).

$$\min_{k_R k'_T,c} \sum_{n=1}^{L} \left\| I_n / I_{R_0,n} - (k_R R_n(c) + k'_T T_n(c)) \right\|_2 \tag{15}$$

Figure 12:
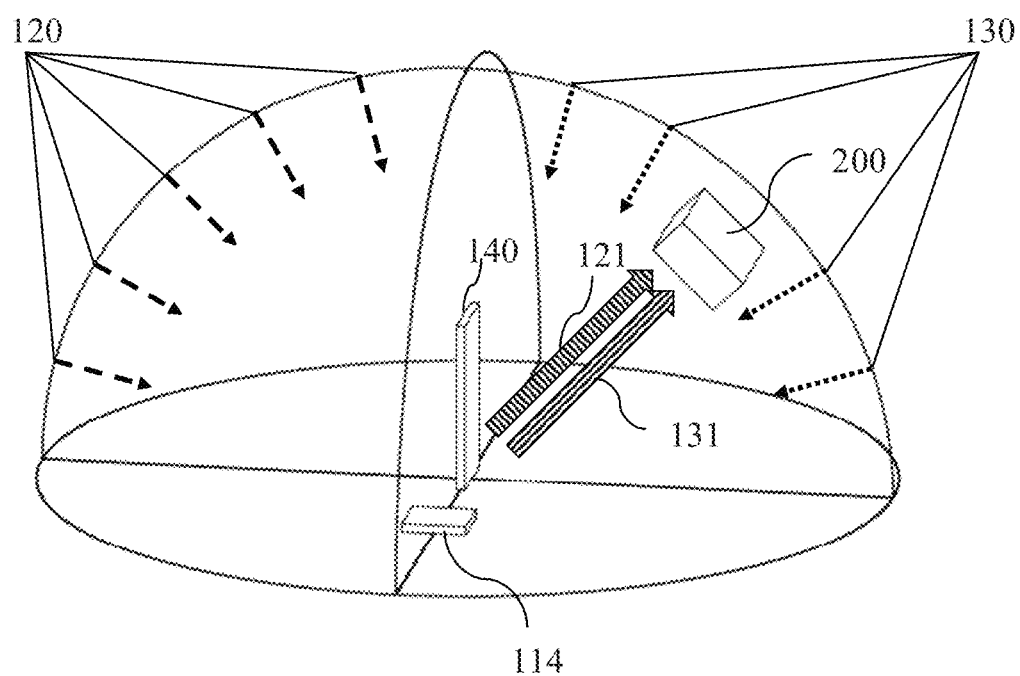
FIG. 12 is an explanatory diagram of a method of acquiring the ambient light information using a standard reflective plate according to the second embodiment.

In the expression (15), $k'_T = m \cdot k_T$, and $R_n(c)$ and $T_n(c)$ use the data of the expressions (7) and (8). The method of acquiring the ambient light information $I_{R0,n}$ is not limited to the above method, and as illustrated in FIG. 12, a standard reflective plate 114 is imaged by the camera 200, and the ambient light information $IR_{0,n}$ may be acquired from the pixel values of the image of the captured standard reflective plate. FIG. 12 is an explanatory diagram of a method of acquiring ambient light information using the standard reflective plate 114.

Figure 13:
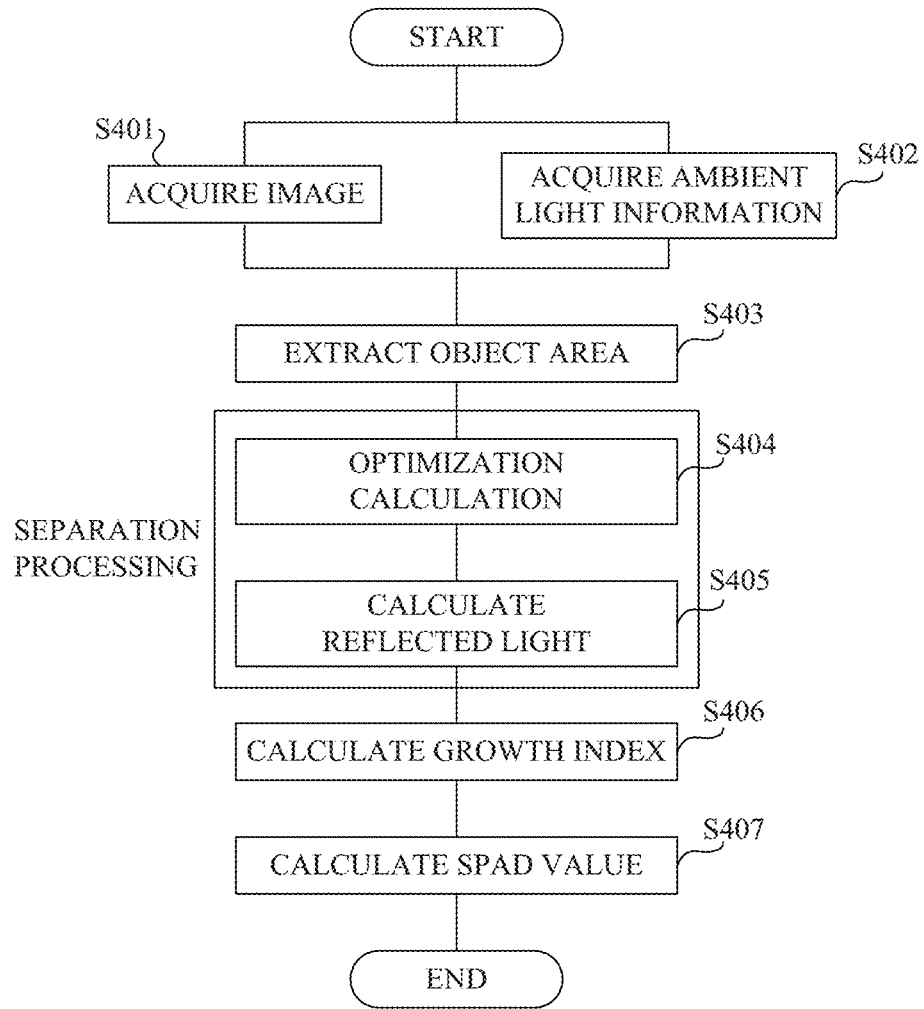
FIG. 13 is a flowchart of an image processing method according to the second embodiment.

Referring now to FIG. 13, a description will be given of the image processing method according to this embodiment. FIG. 13 is a flowchart of the image processing method (SPAD value estimating method) according to this embodiment. Each step in FIG. 13 is mainly executed by the acquiring means 102a or the separating means 102b in the image processor 102.

First, in the step S401, the image capturer 101 in the image processing system 300 images the object 140 in response to the signal from the controller 103 and acquires an RGB image (spectral image). Then, the acquiring means 102a in the image processor 102 acquires the image captured by the image capturer 101. At the same time as the step S401, in the step S402, the ambient light information acquirer 310 (ambient light sensor 113) acquires (detects) the ambient light information (ambient light data) $I_{R0, n}$ when the image is captured in response to the signal from the controller 103. Then, the acquiring means 102a acquires the ambient light information $I_{R0, n}$ detected by the ambient light information acquirer 310.

Next, in the step S403, the image processor 102 extracts the captured area (object area) of the paddy rice as the object 140. As a method for extracting the paddy rice area, for example, an image may be generated by converting an RGB image into an HSV color space, and pixels within a range of hue angles that can be taken by the paddy rice leaves may be extracted as the paddy rice area.

Next, in the steps S405 and S406, the separating means 102b in the image processor 102 performs the separation processing. First, in the step S404, the separating means 102b performs an optimization calculation based on the expression (15) for each pixel of the paddy rice area extracted in the step S403. Next, in the step S405, the separating means 102b calculates the reflected light component $I'_{R, n}$ whose ambient light component is corrected, using the following expression (16) with the ratio $k_R$ of the reflected light and the concentration c calculated in the step S404.

$$I'_{R,n} = I_{R,n}/I_{R0,n} = k_R R_n(c) \quad (16)$$

Next, in the step S406, the image processor 102 calculates NGRDI (Normalized Green Red Difference Index) as an index (growth index) that correlates with the SPAD value. NGRDI is calculated based on the following expression (17) using the reflected light component calculated in the step S405.

$$\text{NGRDI} = (I'_{R,2} - I'_{R,1})/(I'_{R,2} + I'_{R,1}) \quad (17)$$

Finally, in the step S407, the image processor 102 converts NGRDI into a SPAD value using the following expression (18), which is a correlation expression between NGRDI and the SPAD value.

$$\text{SPAD value} = \sum_{i=0}^{N} d_i \text{NGRDI}^i \quad (18)$$

In the expression (18), $d_i$ is a constant representing a correlation between NGRDI and the SPAD value.

In the separation processing according to this embodiment, the material concentration c (corresponding to the SPAD value) is calculated by the optimization calculation of the expression (15), but the calculated material concentration c and the ratio $k_R$ of the reflected light contain errors. Therefore, this embodiment performs processes of the steps S405 to S407 in order to estimate the material concentration with more redundancy.

Figure 14:
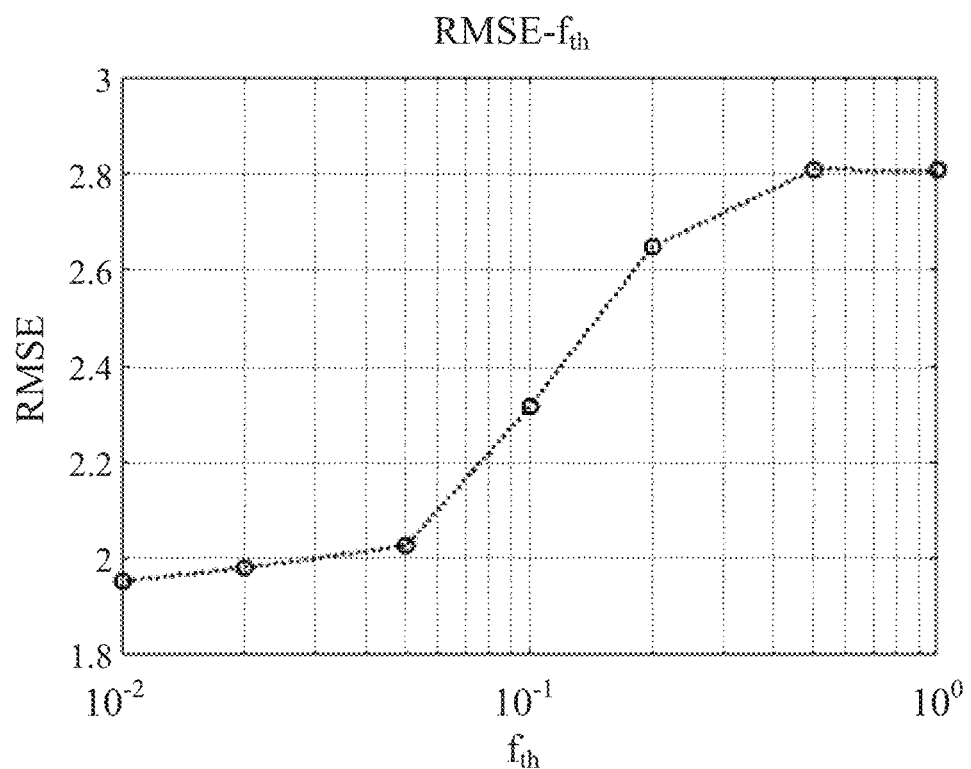
FIG. 14 is an explanatory diagram of a difference in estimation accuracy of a material concentration depending on a threshold according to the second embodiment.

The method according to this embodiment can improve the estimation accuracy of the SPAD value by using to estimate the SPAD value the optimization calculation result of only pixels having values f of the optimization evaluation function of the expression (15) are equal to or less than a threshold $f_{th}$. FIG. 14 is an explanatory diagram of a difference in estimation accuracy of the SPAD value (material concentration) with respect to the threshold $f_{th}$. In FIG. 14, the abscissa axis represents the threshold $f_{th}$, and the ordinate axis represents the root mean square error RMSE between the average value and the correct value of the SPAD value estimation results of the pixels equal to or smaller than the threshold $f_{th}$. As illustrated in FIG. 14, the estimation accuracy of the SPAD value can be improved by properly setting the threshold $f_{th}$.

Figure 15:
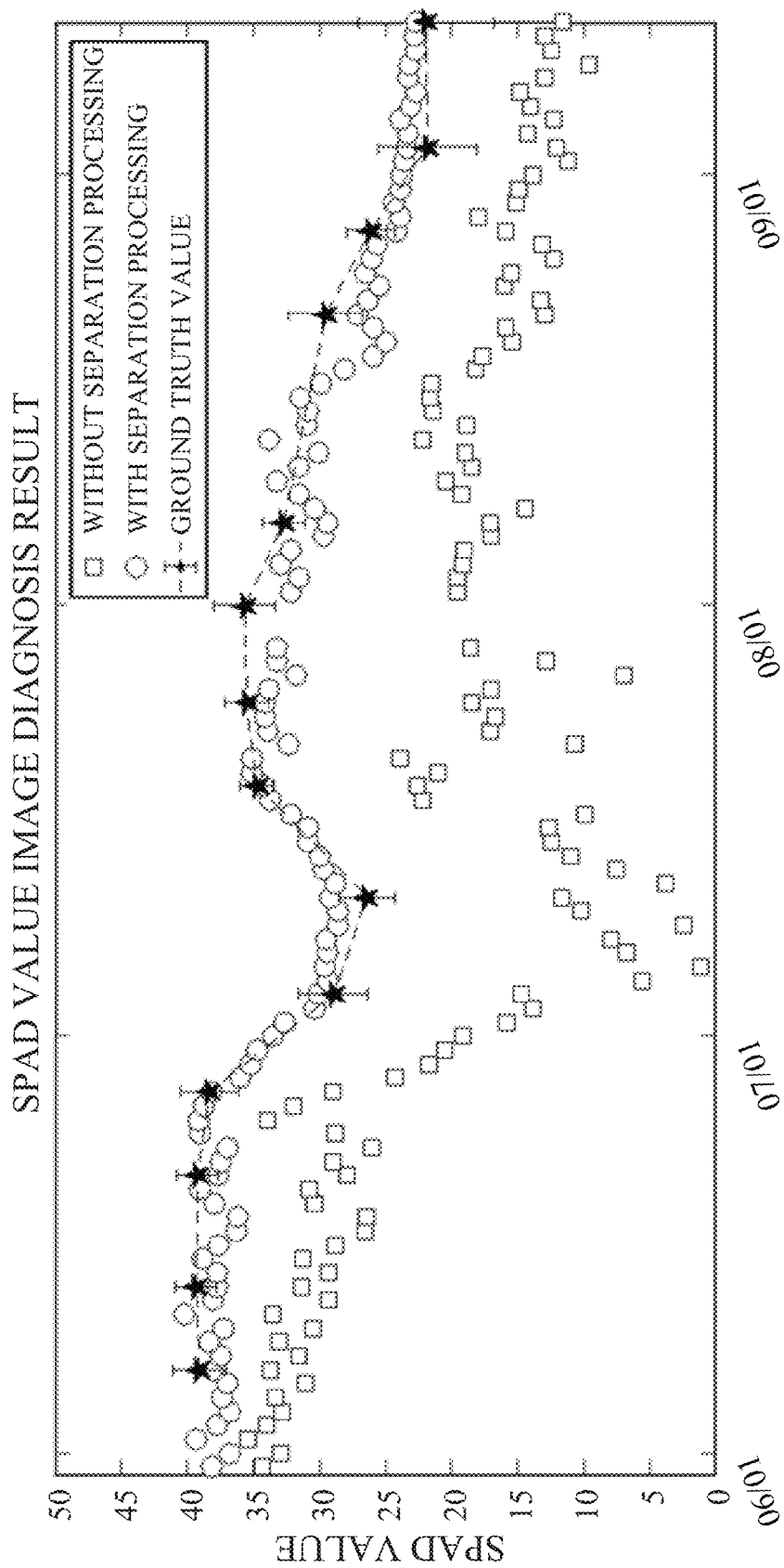
FIG. 15 is an explanatory diagram of a SPAD value estimation result according to the second embodiment.

FIG. 15 is an explanatory diagram of the SPAD value estimation result, and illustrates the result of estimating the daily change of the SPAD value from the RGB image captured by a fixed-point camera. In FIG. 15, the abscissa axis represents the date and the ordinate axis represents the SPAD value. In FIG. 15, a squarely plotted point represents an estimation result when the separation processing according to this embodiment is not performed in the steps S404 and S405, and a dot plotted point represents an estimation result when the separation processing is performed. An asterisk plotted point represents a correct value, and an average value of the results measured by the SPAD meter is adopted as the correct value for 10 strains of paddy rice in the image estimation area. An error bar represents the standard deviation. Therefore, as illustrated in FIG. 15, the separation processing according to this embodiment can quantitatively estimate the material concentration.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Thus, in each embodiment, the image processing apparatus (image processor 102) has the acquiring means 102a and the separating means 102b. The acquiring means acquires the image of the object (spectral image), the ambient light data (information on the tint) when the object is imaged, and the reflection characteristic data ($R_n(c)$) and transmission characteristic data ($T_n(c)$) that depend on the concentration (SPAD value) of the material (chlorophyll, etc.) contained in the object. The separating means separates the reflected light component ($I_{R,n}$) and the transmitting light component ($I_{T,n}$) from the image using the image, the ambient light data, the reflection characteristic data, and the transmission characteristic data. Thereby, the image processing apparatus according to each embodiment can separate the reflected light component and the transmitting light component from the spectral image obtained by imaging the semitransparent object. Therefore, each embodiment can provide an image processing method, an image processing apparatus, an imaging system, and a program, each of which can highly accurately estimate the concentration of a material contained in an object from a spectral image.

The present invention can provide an image processing method, an image processing apparatus, an imaging system, and a program, each of which can highly accurately estimate a concentration of a material contained in an object from a spectral image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

In particular, in each embodiment, a paddy rice leaf were taken as an example as an object, but it can also be applied to another object. In each embodiment, the RGB spectral image is captured as an example, but each embodiment is also applicable to a multiband image and a hyperspectral image having four or more spectral wavelengths. In each embodiment, the image capturer and the ambient light information acquirer are separated from each other, but the image capturer and the ambient light information acquirer may be integrated with each other. The evaluation function for the optimization is not limited to the expressions (2) and (15) and, for example, the L1 norm may be used instead of the L2 norm. Each embodiment illustratively executes the optimization calculation in the image processing apparatus, but the optimization calculation with heavy processing may be executed on the cloud computing.

What is claimed is:

1. An image processing method comprising:
acquiring an image obtained by imaging of an object, ambient light data during the imaging, and reflection characteristic data and transmission characteristic data which depend on a concentration of a material contained in the object;
separating a reflected light component and a transmitting light component in the image using the ambient light data, the reflection characteristic data, and the transmission characteristic data; and
estimating a concentration of a material contained in the object based on the separated reflected light component and transmitting light component in the image,
wherein the separating includes optimizing for acquiring, through optimization, a ratio of the reflected light component and a ratio of the transmitting light component to a luminance value of the image,
wherein the ambient light data includes first illuminance information acquired by a first ambient light sensor and second illuminance information acquired by a second ambient light sensor, and
wherein the optimizing performs the optimization using the following expression:

$$\min_{k_R k_T, c} \sum_{n=1}^{L} \left\| I_n - \left( k_R I_{R_0,n} R_n(c) + k_T I_{T_0,n} T_n(c) \right) \right\|_2$$

where $I_n$ is the luminance value of the image, $I_{T0,n}$ is the first illuminance information, $I_{R0,n}$ is the second illuminance information, c is the concentration of the material, $R_n(c)$ is the reflection characteristic data, and $T_n(c)$ is the transmission characteristic data, $k_R$ is the ratio of the reflected light component, and $k_T$ is the ratio of the transmitting light component.

2. An image processing method comprising:
acquiring an image obtained by imaging of an object, ambient light data during the imaging, and reflection characteristic data and transmission characteristic data which depend on a concentration of a material contained in the object;
separating a reflected light component and a transmitting light component in the image using the ambient light data, the reflection characteristic data, and the transmission characteristic data, wherein the separating includes optimizing for acquiring, through optimization, a ratio of the reflected light component and a ratio of the transmitting light component to a luminance value of the image; and
estimating a concentration of a material contained in the object based on the separated reflected light component and transmitting light component in the image,
wherein the ambient light data is illuminance information acquired by an ambient light sensor, and
wherein the optimizing performs the optimization using the following expression:

$$\min_{k_R k_T, c} \sum_{n=1}^{L} \left\| I_n - \left( k_R I_{TR_0,n} R_n(c) + k_T I_{TR_0,n} T_n(c) \right) \right\|_2$$

where $I_n$ is the luminance value of the image, $I_{T0,n}$ is the first illuminance information, $I_{R0,n}$ is the second illuminance information, c is the concentration of the material, $R_n(c)$ is the reflection characteristic data, and $T_n(c)$ is the transmission characteristic data, $k_R$ is the ratio of the reflected light component, and $k_T$ is the ratio of the transmitting light component.

3. The image processing method according to claim 1, wherein the separating includes calculating at least one of the reflected light component or the transmitting light component using the ratio of the reflected light component, the ratio of the transmitting light, and the concentration of the material.

4. The image processing method according to claim 1, wherein the reflection characteristic data and the transmission characteristic data are a function of the concentration of the material.

5. The image processing method according to claim 4, wherein the reflection characteristic data and the transmission characteristic data are differentiable with respect to the concentration of the material.

6. The image processing method according to claim 1, wherein the object is a leaf of a plant and the material is chlorophyll.

7. An image processing apparatus comprising:
at least one processor or circuit configured to execute a plurality of tasks including:
an acquiring task of acquiring an image obtained by imaging of an object, ambient light data during the imaging, and reflection characteristic data and transmission characteristic data which depend on a concentration of a material contained in the object;
a separating task of separating a reflected light component and a transmitting light component in the image using the ambient light data, the reflection characteristic data, and the transmission characteristic data; and
estimating a concentration of a material contained in the object based on the separated reflected light component and transmitting light component in the image,
wherein the separating task acquires, through optimization, a ratio of the reflected light component and a ratio of the transmitting light component to a luminance value of the image,
wherein the ambient light data includes first illuminance information acquired by a first ambient light sensor and second illuminance information acquired by a second ambient light sensor, and
wherein the separating task performs the optimization using the following expression:

$$\min_{k_R k_T, c} \sum_{n=1}^{L} \left\| I_n - (k_R I_{R_0, n} R_n(c) + k_T I_{T_0, n} T_n(c)) \right\|_2$$

where $I_n$ is the luminance value of the image, $I_{T0, n}$ is the first illuminance information, $I_{R0, n}$ is the second illuminance information, c is the concentration of the material, $R_n(c)$ is the reflection characteristic data, and $T_n(c)$ is the transmission characteristic data, $k_R$ is the ratio of the reflected light component, and $k_T$ is the ratio of the transmitting light component.

8. An image processing apparatus comprising:
at least one processor or circuit configured to execute a plurality of tasks including:
an acquiring task of acquiring an image obtained by imaging of an object, ambient light data during the imaging, and reflection characteristic data and transmission characteristic data which depend on a concentration of a material contained in the object;
a separating task of separating a reflected light component and a transmitting light component in the image using the ambient light data, the reflection characteristic data, and the transmission characteristic data; and
estimating a concentration of a material contained in the object based on the separated reflected light component and transmitting light component in the image,
wherein the separating task acquires, through optimization, a ratio of the reflected light component and a ratio of the transmitting light component to a luminance value of the image,
wherein the ambient light data is illuminance information acquired by an ambient light sensor, and
wherein the separating task performs the optimization using the following expression:

$$\min_{k_R k_T, c} \sum_{n=1}^{L} \left\| I_n - (k_R I_{TR_0, n} R_n(c) + k_T I_{TR_0, n} T_n(c)) \right\|_2$$

is the luminance value of the image, $I_{TR0, n}$ is the illuminance information, c is the concentration of the material, $R_n(c)$ is the reflection characteristic data, and $T_n(c)$ is the transmission characteristic data, $k_R$ is the ratio of the reflected light component, and $k_T$ is the ratio of the transmitting light component.

9. The image processing apparatus according to claim 7, wherein the separating task includes a task of calculating at least one of the reflected light component or the transmitting light component using the ratio of the reflected light component, the ratio of the transmitting light, and the concentration of the material.

10. The image processing apparatus according to claim 7, wherein the reflection characteristic data and the transmission characteristic data are a function of the concentration of the material.

11. The image processing apparatus according to claim 10, wherein the reflection characteristic data and the transmission characteristic data are differentiable with respect to the concentration of the material.

12. The image processing apparatus according to claim 7, wherein the object is a leaf of a plant and the material is chlorophyll.

13. An imaging system comprising:
an image capturing circuit configured to capture an object;
a light detecting circuit configured to detect ambient light data when the object is captured by the image capturing circuit; and
the image processing apparatus according to claim 7.

14. The imaging system according to claim 13, wherein the light detecting circuit exclusively includes a single ambient light sensor, and
wherein the ambient light data has illuminance information detected by the single ambient light sensor.

15. A non-transitory computer-readable storage medium storing a computer program that causes a computer to execute the image processing method according to claim 1.

* * * * *